(12) United States Patent
McCaffrey (10) Patent No.: US 8,584,849 B2
(45) Date of Patent: Nov. 19, 2013

(54) TRAY FOR LOADING A MEDICAL DEVICE

(75) Inventor: Gerry McCaffrey, Tuam (IE)

(73) Assignee: Medtronic Ventor Technologies Ltd., Minneapolis, MN (US)

( * ) Notice: Subject to any disclaimer, the term of this patent is extended or adjusted under 35 U.S.C. 154(b) by 307 days.

(21) Appl. No.: 12/914,315

(22) Filed: Oct. 28, 2010

(65) Prior Publication Data

US 2012/0103840 A1 May 3, 2012

(51) Int. Cl.
*A61B 19/00* (2006.01)

(52) U.S. Cl.
USPC .......................................... 206/364; 206/438

(58) Field of Classification Search
USPC ......... 206/364, 363, 438, 210, 564; D24/229, D24/234; 623/1.11
See application file for complete search history.

(56) References Cited

U.S. PATENT DOCUMENTS

| | | | | |
|---|---|---|---|---|
| D221,035 S | * | 6/1971 | Raines | D24/230 |
| 3,851,649 A | * | 12/1974 | Villari | 206/438 |
| 4,160,505 A | * | 7/1979 | Rauschenberger | 206/571 |
| 4,226,328 A | * | 10/1980 | Beddow | 206/364 |
| D262,995 S | * | 2/1982 | Gaba et al. | D24/229 |
| 4,779,727 A | | 10/1988 | Taterka et al. | |
| 5,098,391 A | | 3/1992 | Pantages et al. | |
| 5,156,267 A | * | 10/1992 | Yates et al. | 206/364 |
| 5,178,267 A | | 1/1993 | Grabenkort et al. | |
| 5,353,929 A | * | 10/1994 | Foster | 206/364 |
| 5,526,928 A | * | 6/1996 | Yabe et al. | 206/364 |
| 5,779,053 A | * | 7/1998 | Partika et al. | 206/570 |
| 5,848,691 A | | 12/1998 | Morris et al. | |
| 5,947,284 A | * | 9/1999 | Foster | 206/364 |
| 6,068,121 A | | 5/2000 | McGlinch | |
| D480,816 S | * | 10/2003 | McMichael et al. | D24/229 |
| 7,278,987 B2 | * | 10/2007 | Solazzo | 604/356 |
| 7,712,606 B2 | | 5/2010 | Salahieh et al. | |
| 2004/0243214 A1 | | 12/2004 | Farrell et al. | |
| 2005/0098460 A1 | * | 5/2005 | Smith et al. | 206/366 |
| 2005/0278012 A1 | | 12/2005 | Vonderwalde | |
| 2006/0004469 A1 | | 1/2006 | Sokel | |
| 2006/0282045 A1 | * | 12/2006 | Wilkinson et al. | 604/198 |
| 2007/0095679 A1 | * | 5/2007 | Nakamura | 206/210 |
| 2010/0307941 A1 | * | 12/2010 | Tomes et al. | 206/366 |

\* cited by examiner

*Primary Examiner* — David Fidei (57) ABSTRACT

An embodiment of the present invention includes a tray and a method for loading a medical device on a catheter assembly. The tray can include a tray body defining a first receptacle for seating the handle assembly of the catheter assembly, an elongate receptacle for seating a delivery shaft of the catheter assembly, and a reservoir for holding a fluid. A portion of the elongate receptacle slopes downward towards the reservoir. The reservoir has a bottom surface that is below a portion of the elongate receptacle that is contiguous with the reservoir. Accordingly, when the reservoir is filled with a fluid and the catheter assembly is seated in the first receptacle and the elongate receptacle, the distal tip of the catheter assembly is submerged in the fluid in the reservoir. The tray body is also configured to prevent movement of a catheter assembly seated therein.

4 Claims, 6 Drawing Sheets

TRAY FOR LOADING A MEDICAL DEVICE

BACKGROUND OF THE INVENTION

1. Field of the Invention

The present invention relates to catheter assemblies, loading trays, and methods of loading a catheter assembly. More specifically, the present invention relates to loading trays that improve the process of loading a medical device on a catheter assembly.

2. Background

Recently, minimally invasive approaches have been developed to facilitate catheter-based implantation of valve prostheses on the beating heart. These approaches eliminate the use of classical sternotomy and cardiopulmonary bypass. For example, French Patent Application No. 99 14462 illustrates a technique and a device for the ablation of a deficient heart valve by percutaneous route, with a peripheral valvular approach. Published International Application (PCT) Nos. WO 93/01768 and WO 97/28807, as well as U.S. Pat. No. 5,814,097 to Sterman et al., U.S. Pat. No. 5,370,685 to Stevens, and U.S. Pat. No. 5,545,214 to Stevens illustrate techniques that are minimally invasive as well as instruments for carrying out these techniques.

A valve prosthesis formed by attaching a valve to a frame made of a wire or a network of wires has been proposed. Such a valve prosthesis can be contracted radially to introduce the valve prosthesis into the body of the patient percutaneously through a catheter. The valve prosthesis can be deployed by radially expanding it once positioned at the desired target site. U.S. Pat. No. 3,657,744 to Ersek discloses a cylindrical, frame-supported, tri-leaflet tissue heart valve that can be delivered through a catheter assembly. The valve prosthesis is mounted onto a distal tip of the catheter assembly prior to delivery to the target location where the valve prosthesis is expanded into place.

Current techniques for delivering prosthetic heart valves through a catheter assembly include a transapical approach for aortic valve replacement. A crimped, valve prosthesis reversibly coupled to a distal tip of a delivery catheter assembly is transcatheterally advanced toward the native valve, where it is either forcefully deployed using a balloon catheter, or, alternatively, passively deployed using a self-expandable system. Accurate positioning of the replacement valve in the native annulus is critical to the success of the implantation.

To prepare such a valve prosthesis for implantation, the valve prosthesis can be initially provided in an expanded or uncrimped condition, then crimped or compressed around the distal tip of the catheter assembly until the valve prosthesis is as close to the diameter of the distal tip as possible. Various methods and devices are available for crimping the valve prosthesis onto the catheter's distal tip, which may include hand-held devices or tabletop devices, for example. These crimping devices can initially provide an opening that is large enough to accommodate a valve prosthesis in its expanded condition and be positioned over a desired section of a distal tip of the catheter assembly. This valve prosthesis can then be compressed by reconfiguring the opening of the crimping device to uniformly decrease the size of the opening until the valve is compressed to the desired size.

Loading a valve prosthesis on the catheter assembly, however, can be difficult as the valve prosthesis and crimping device must be carefully inserted over the distal tip of the catheter assembly without damaging the valve. Damage to the valve should be avoided. Accordingly, there is a need for a loading apparatus that securely holds the catheter assembly without use of a user's hands. Such restraint would allow a user to carefully align the valve prosthesis with the distal tip of the catheter assembly with two hands.

Further, the entire process of crimping and loading a valve prosthesis onto a catheter assembly, including crimping the valve prosthesis with the crimping device, positioning the prosthesis valve and the crimping accessory on the catheter assembly, and removing the crimping accessories from the catheter assembly should be performed in a saline bath that submerges the valve prosthesis. Submerging the valve prosthesis in the saline bath reduces risk that the valve prosthesis will be contaminated before being introduced into the body. According, there is a need for a loading tray that ensures that any user of a catheter assembly loads the valve prosthesis under the optimal conditions.

BRIEF SUMMARY OF THE INVENTION

In an embodiment of the present invention, a tray for loading a medical device on a catheter assembly comprises a tray body defining a first receptacle for seating the handle assembly of the catheter assembly, an elongate receptacle for seating a delivery shaft of the catheter assembly, and a reservoir for holding a fluid. The elongate receptacle slopes downward from the first receptacle for at least a portion of the elongate receptacle. The reservoir has a bottom surface that is below the portion of the elongate receptacle that is contiguous with the reservoir. Accordingly, when the reservoir is filled with a fluid and the catheter assembly is seated in the first receptacle and the elongate receptacle, the distal tip of the catheter assembly is submerged in the fluid in the reservoir. The tray body is also configured to prevent movement of a catheter assembly seated therein.

The first receptacle, the elongate receptacle, and the reservoir can be linearly aligned. The contour of the first receptacle can substantially match the contour of a portion of the handle assembly of the catheter assembly. At least one protrusion can extend from the surface defining the elongate receptacle to create a snap fit with the delivery shaft of the catheter.

In another embodiment, the tray can also include at least one receptacle for closely seating the catheter assembly. The additional receptacle is separate from the first receptacle, the elongate receptacle, and the reservoir.

In an embodiment, a method for loading a medical device on a catheter assembly includes seating the handle assembly of the catheter assembly in the first receptacle, seating the delivery shaft of the catheter assembly in the elongate receptacle, and filling the reservoir with a fluid. When the catheter assembly is seated in the tray body, the distal tip of the catheter assembly is submerged in the fluid in the reservoir. The method can include loading a valve prosthesis on the distal tip of the catheter assembly while the valve prosthesis and the distal tip are submerged in the reservoir. The method can also include implanting the loaded valve prosthesis. Additionally, the method can include crimping the valve prosthesis while submerged in the reservoir. The method can include removing the catheter assembly from a second receptacle in which the catheter assembly is seated.

BRIEF DESCRIPTION OF THE FIGURES

The accompanying figures, which are incorporated herein, form part of the specification and illustrate an embodiment of a tray and method for loading a medical device on a catheter assembly. Together with the description, the figures further serve to explain the principles of and to allow a person working in the field to make and use the tray and method of loading a medical device on a catheter assembly. In the drawings, like reference numbers indicate identical or functionally similar elements.

DETAILED DESCRIPTION OF THE INVENTION

The following is a detailed description of a tray and a method for loading a medical device on a catheter assembly. Other embodiments are possible. Modifications can be made to the embodiments described herein without departing from the spirit and scope of the present invention. Therefore, the following detailed description is not meant to be limiting. Further, the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

In an embodiment, a tray 22 is configured to be used with a catheter assembly 10 as illustrated in FIGS. 1 and 4-6. Catheter assembly 10 generally includes a handle assembly 16 located at a proximal end 12 of catheter assembly 10, a distal tip assembly 20 located at a distal end 14 of catheter assembly 10, and a delivery shaft 18 between distal tip assembly 20 and handle assembly 16. Handle assembly 16 can include one or more flushing ports 13 that can be used to de-air catheter assembly 10 and to introduce a fluid into the target area. The delivery shaft 18 can include a tubular flexible braided structure and an introducer slidably located along the braided structure. Deliver shaft 18 can have a flushing port 19.

It is understood that catheter assembly 10 is merely an exemplary embodiment of a catheter assembly that can be used in conjunction with a loading tray 22 according to the present invention. The present invention is not limited to loading trays that can be used with catheter assemblies as the one described herein. Tray 22 and methods described herein can be used with catheter assemblies having different types of handle assemblies, delivery shafts, and distal tips, including, e.g., conventional hand controlled catheter assemblies.

Figure 1:
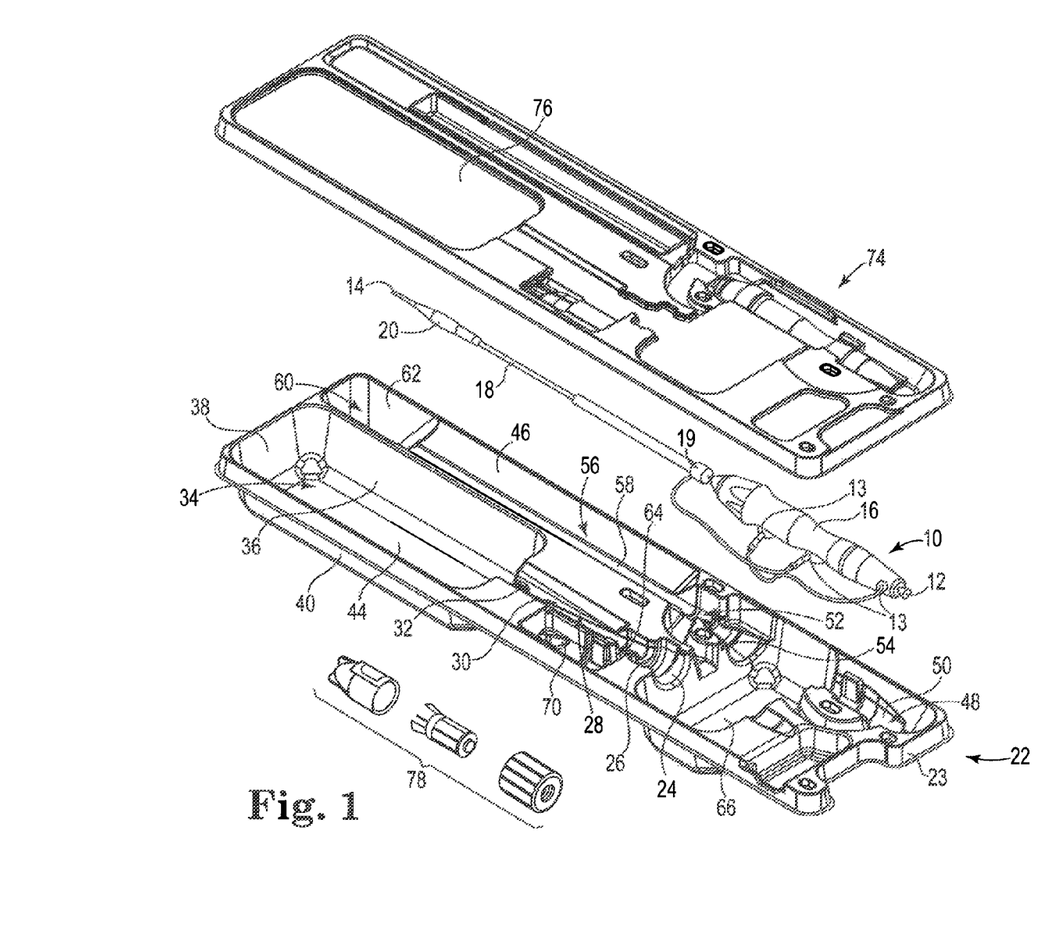
FIG. 1 is an exploded perspective view of a catheter assembly and a loading tray and accompanying lid according to an embodiment of the present invention.
Figure 2:
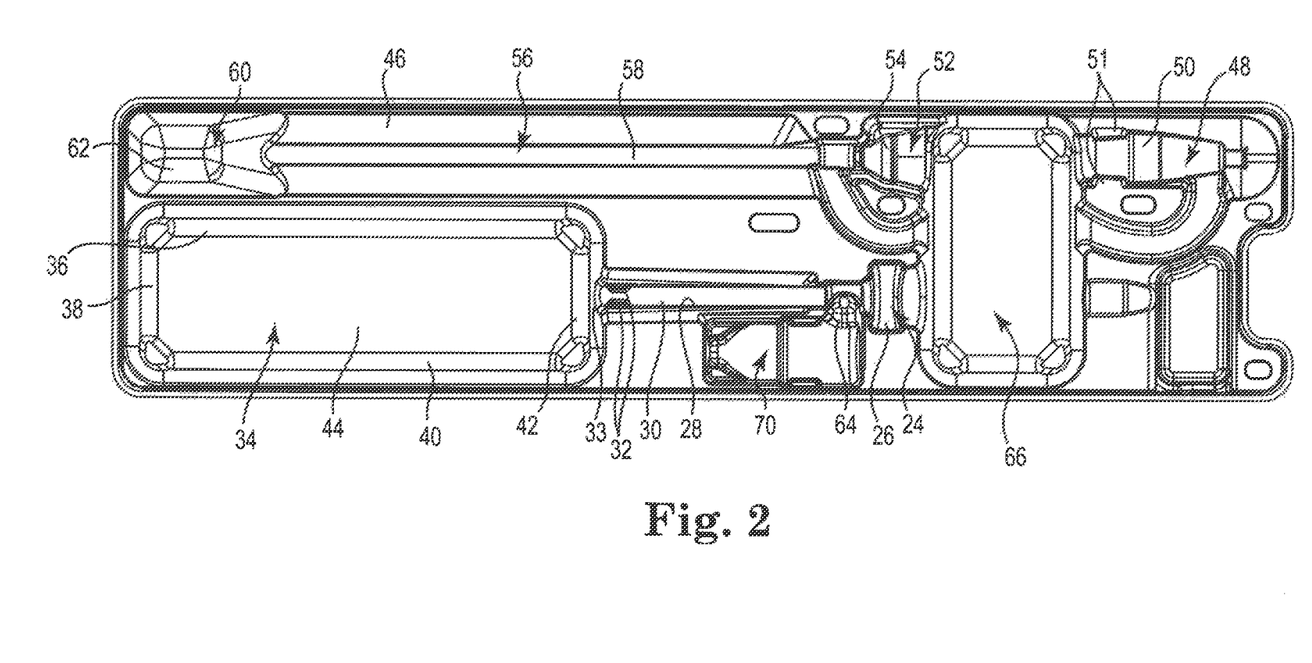
FIG. 2 is a top view of the loading tray of FIG. 1.
Figure 3:
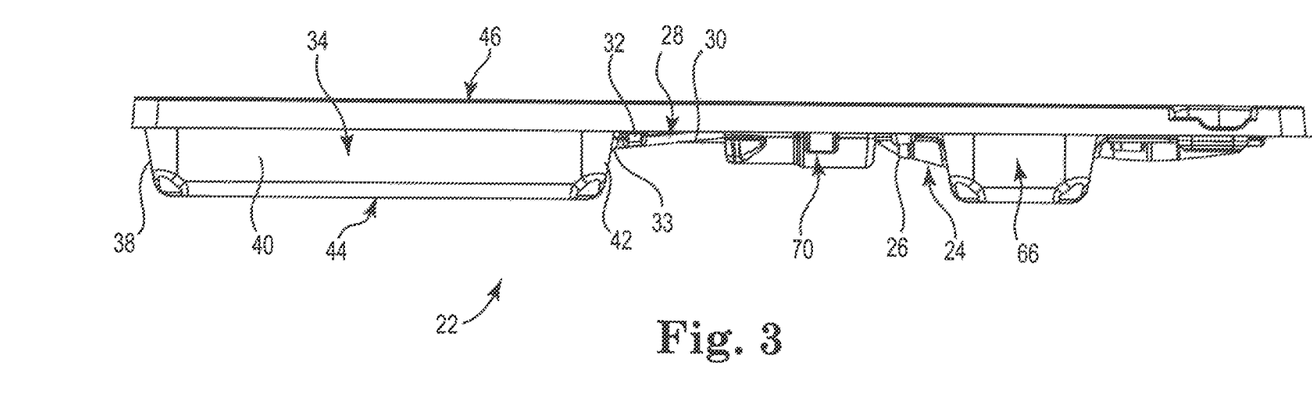
FIG. 3 is a side view of the loading tray of FIGS. 1-2.
Figure 4:
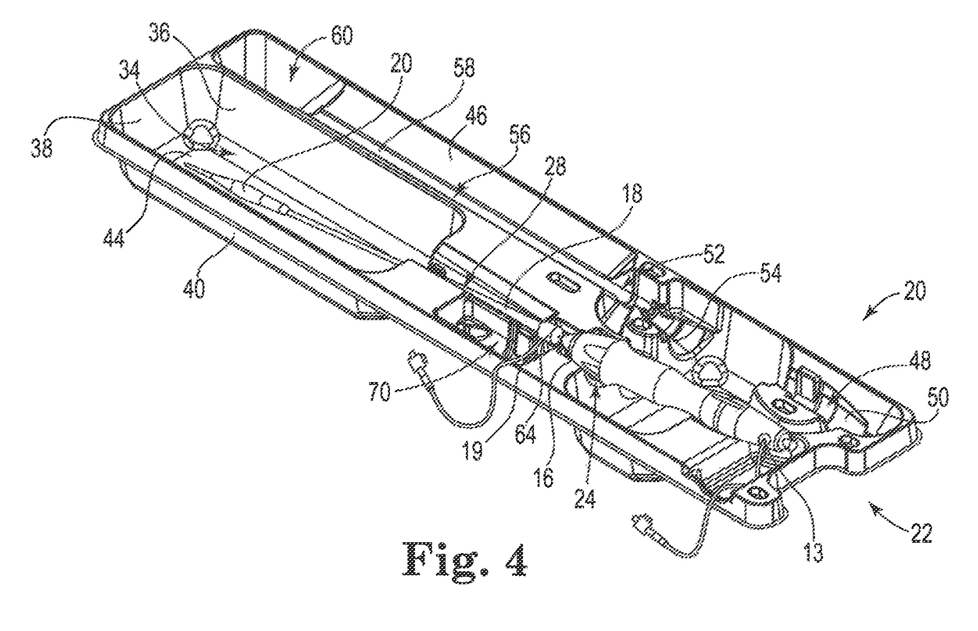
FIG. 4 is a perspective view of the tray of FIGS. 1-3 with a catheter assembly seated therein for loading.
Figure 5:
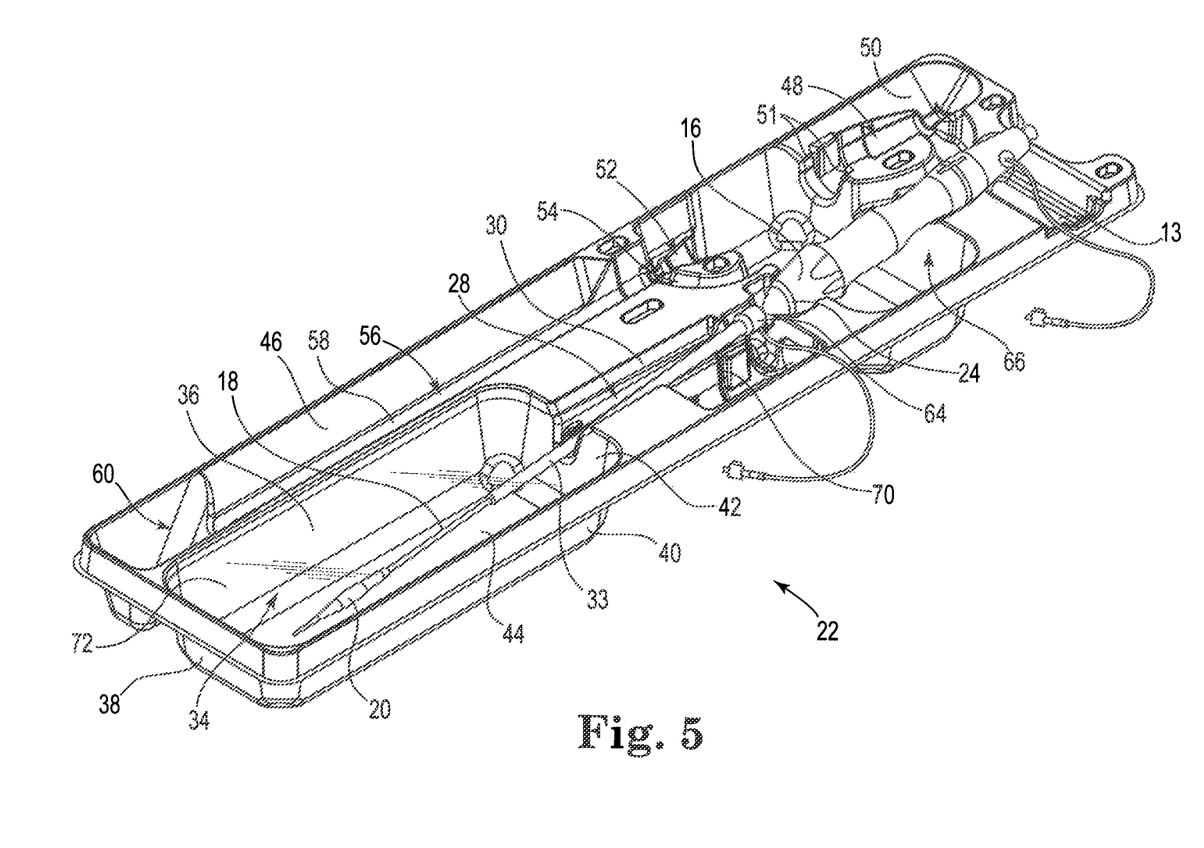
FIG. 5 is a perspective view of the tray of FIGS. 1-4 with a catheter assembly seated therein and a reservoir filled with a fluid for loading.

In an embodiment, tray 22 is made of a tray body 23 defining a handle assembly receptacle 26 for seating handle assembly 16 of catheter assembly 10, an elongate delivery shaft receptacle 28 for seating delivery shaft 18 of catheter assembly 10, and a reservoir 34 for holding a fluid 72 (shown in FIG. 5). Delivery shaft receptacle 28 slopes downward towards reservoir 34 for at least a portion of delivery shaft receptacle 28. Reservoir 34 has a bottom surface 44 that is below a portion of delivery shaft receptacle 28 that is contiguous reservoir 34. When reservoir 34 is filled with a fluid 72 and handle assembly 16 is seated in the handle assembly receptacle 24, distal tip 20 is submerged in the fluid in reservoir 34. Tray body 23 is configured to prevent movement, including but not limited to, translation and rotation, of catheter assembly 10 seated therein. FIGS. 1-6 illustrate tray 22 according to an embodiment of the present invention.

In the illustrated embodiment, tray 22 can include tray body 23. Tray body 23 can be made of various polymer materials including, for example, Polyethylene Terephthalate Glycol (PETG). Tray body 23 can be molded and have a thickness of approximately 1.0-1.4 mm. The present invention, however, is not limited to polymer materials and can include other suitable materials, for example, stainless steel.

Tray body 23 can include a top surface 46. Top surface 46 generally defines the uppermost horizontal plane of loading tray 22. In the illustrated embodiment, other components of tray 22 do not extend above top surface 46.

Tray body 23 can define a handle assembly receptacle 24 for seating at least a portion of the handle assembly 16. Handle assembly receptacle 24 is defined by a generally arcuate surface 26. Surface 26 extends downward from top surface 46. The contour of surface 26 generally corresponds to at least a portion of the contour of handle assembly 16. For example, as illustrated, surface 26 corresponds to the contour of the distal portion of handle assembly 16. However, the contour of surface 26 can correspond to other portions of handle assembly 16 or delivery shaft 18.

Tray body 23 can also define an elongate delivery shaft receptacle 28 for seating delivery shaft 18 during loading. Delivery shaft receptacle 28 is defined by surface 30 that is generally U-shaped or arcuate and extends downward from top surface 46. On one end, delivery shaft receptacle 28 is contiguous with handle assembly receptacle 24. Delivery shaft receptacle 28 slopes downward towards reservoir 34 for at least a portion of the delivery shaft receptacle 28. On the other end, delivery shaft receptacle 24 is contiguous with reservoir 34 at edge 33. The angle of delivery shaft receptacle 24 inclines at least a portion of seated catheter assembly 10 downward such that distal tip 20 is below the downward sloped portion of delivery shaft 18.

In one embodiment, extending from surface 30 towards the center of delivery shaft receptacle 28 is a pair of opposing protrusions 32. Protrusions 32 are sized so that the opening between the protrusions is slightly smaller than the width of delivery shaft 18. When downward force is applied to delivery shaft 18 that is engaged with protrusions 32, delivery shaft 18 snaps into delivery shaft receptacle 28. This snap fit secures catheter assembly 10 within tray 22 during loading by preventing the catheter assembly from moving, including pivoting about handle assembly receptacle 24 from the weight of handle assembly 16 and upward translation. The contour of handle assembly receptacle 24 or delivery shaft receptacle 28 prevents downward and horizontal translation. This restraint securely maintains distal tip 20 of catheter assembly 10 within the reservoir 34 during loading.

Although the protrusions 32 are illustrated in delivery shaft receptacle 28, the present invention is not limited to protrusion located within receptacle 28. An embodiment of the present invention can include protrusions located in handle assembly receptacle 24. Further, the present invention is not limited to tray 22 that has a snap fit. For example, tray body 23 can define receptacles sized to have a friction fit with portions of catheter assembly 10.

Surface 30 can define an opening 64 on one side of delivery shaft receptacle 28. Opening 64 is located at a position along delivery shaft receptacle 28 such that when catheter assembly 10 is seated in tray body 23, flushing port 19 is aligned with opening 64, which allows catheter assembly 10 to seat flush within tray body 23. It is understood that not all catheters have flushing ports and therefore opening 64 is an optional embodiment. Tray body 23 can further define optional receptacle 70. Receptacle 70 is adjacent opening 64. Receptacle 70 can be sized and shaped to create a snap-fit or a friction fit with a crimping device 78. Crimping device 78 can be stored in receptacle 70 during transport.

Tray body 23 can further define reservoir 34 that is a recess in top surface 46. In one embodiment, reservoir 34 can be defined by a right wall 36, a back wall 38, a left wall 40, and a front wall 42 that extend downward from top surface 46 to a horizontal bottom surface 44 to form a rectangular recess. As best illustrated in FIG. 3, bottom surface 44 can be below edge 33 and a portion of elongate delivery shaft receptacle 28 that is contiguous with the reservoir 34. The depth of the reservoir 34 may vary depending upon the depth necessary to load a medical device on distal tip 20 while submerged in fluid 72 in reservoir 34. For example, when tray 22 is used to load a heart valve prosthesis on a catheter assembly 10, the depth of reservoir 34 can be approximately 62-68 mm. Although reservoir 34 is rectangular in the illustrated embodiment, the present invention includes a tray that defines reservoirs having other shapes, for example, hemispheres, squares, and cylinders.

Handle assembly receptacle 24, delivery shaft receptacle 28, and reservoir 34 can be aligned linearly such that when catheter assembly 10 is seated in tray body 23, the catheter assembly 10 is in a straight line. The midpoints of handle assembly receptacle 24, delivery shaft receptacle 28, and reservoir 34 can also be co-linear. However, the present invention is not limited to trays having linearly aligned receptacles as embodiments of the present invention can include receptacle alignments that seat the catheter assembly 10 in a bent or curved configuration. Although in the illustrated embodiment, delivery shaft receptacle 28 slopes continuously downward from handle assembly receptacle 24, it is understood that the present invention includes other embodiments having different elevation profiles in which bottom surface 44 is below at least a portion of delivery shaft receptacle 28 that is contiguous with reservoir 34. For example, delivery shaft receptacle 28 can initially slope up from handle assembly receptacle 24 and then slope down towards reservoir 34.

Tray body 23 can also define a gripping receptacle 66 that is contiguous with handle assembly receptacle 24 on the side opposite to the delivery shaft receptacle 28. Gripping receptacle 66 is sized to allow a user's fingers to easily wrap around handle assembly 16 when catheter assembly 10 is seated in the tray body 23 for either loading or transporting.

In another embodiment, tray body 23 can further include at least one receptacle for securing catheter assembly 10 during transport that is separate from reservoir 34, delivery shaft receptacle 28, and handle assembly receptacle 24. In the illustrated embodiment, tray body 23 can define a front handle assembly receptacle 48 for seating a proximal portion of handle assembly 16. Front handle assembly receptacle 48 is defined by a generally arcuate surface 50 that extends downward from top surface 46. Surface 50 can have a contour that corresponds generally to the contour of handle assembly 16 at proximal end 12. A pair of opposing protrusions 51 can extend from surface 50 toward the center of front handle assembly receptacle 48. Protrusions 51 are sized so that the opening between the protrusions is slightly smaller than the width of the proximal portion of handle assembly 16. When pressure is applied against handle assembly 16 that is engaged with protrusions 51, handle assembly 16 snaps in the receptacle 48. This snap fit prevents movement, including vertical translation, and disengagement during transport.

Tray body 23 can also include a back handle assembly receptacle 52 for seating another portion of handle assembly 16 during transport. Back handle assembly receptacle 52 is defined by generally arcuate surface 54 that is recessed downward from top surface 46. Surface 54 can have a contour that corresponds generally to the contour of handle assembly 16 at the handle assembly's distal end. In the illustrated embodiment, front handle assembly receptacle 48 and back handle assembly 52 are separated by gripping receptacle 66. This orientation allows a user to easily grab handle assembly of catheter assembly 10 to unseat catheter assembly 10 after transport.

Tray body 23 can include a delivery shaft receptacle 56 for seating delivery shaft 18 during transport. Delivery shaft receptacle 56 is defined by generally U-shaped or arcuate surface 58 that extends downward from top surface 46. When handle assembly 16 is seated in front handle assembly receptacle 48 and back handle assembly receptacle 52, the delivery shaft 18 passes through delivery shaft receptacle 56. On one end, delivery shaft receptacle 56 is contiguous with back handle assembly receptacle 52.

Tray 22 can also include a distal tip receptacle 60 for protecting distal tip 20 during transport. Distal tip receptacle 60 is defined by concave surface 62 that extends downward from upper surface 46. When catheter assembly 10 is seated, distal tip 20 is enclosed by distal tip receptacle 60.

Although the protrusions 51 are illustrated in front handle assembly receptacle 48, the present invention is not limited to protrusions located within front handle assembly receptacle 48. An embodiment of the present invention can include protrusions located in back handle assembly receptacle 52 or delivery shaft receptacle 56. Further, the present invention is not limited to tray 22 that has a snap fit for securing catheter assembly 10 during transport. Alternatively, tray body 23 can define at least one receptacle sized to have a friction fit with at least one portion of catheter assembly 10 to prevent movement during transport.

In another embodiment, a lid 74 can accompany tray 22. Lid 74 has a lid body 76 configured to fit over the top of tray body 23 when a catheter assembly 10 is seated in front handle assembly receptacle 48, back handle assembly receptacle 52, and delivery shaft receptacle 56. Lid body 76 is contoured to match portions of catheter assembly 10 and tray body 23. Lid 74 securely maintains catheter assembly 10 and other devices, for example, crimping device 78, within tray 22 during transport.

In an embodiment of the present invention, a method for loading a medical device on a catheter assembly comprises seating handle assembly 16 of catheter assembly 10 in handle assembly receptacle 24 in tray body 23, seating delivery shaft 18 of catheter assembly 10 in elongate receptacle 28; and filling reservoir 34 with a fluid 72. FIGS. 4-5 illustrates an embodiment of tray 22 with a catheter assembly 10 seated therein for loading. Distal tip 20 of catheter assembly 10 is suspended within reservoir 34. Distal tip 20 is below the horizontal plane defined by top surface 46 and above the bottom surface 44 of reservoir 34. Accordingly, when reservoir 34 is filled with a fluid 72, as illustrated in FIG. 5, distal tip 20 is submerged in fluid 72. Fluid 72 can be any fluid used during medical procedures, for example, a saline solution.

To seat catheter assembly 10 in the illustrated embodiment of tray body 23, the distal portion of handle assembly 16 is aligned with the matching contour of surface 26, and delivery shaft 18 is aligned with delivery shaft receptacle 28. Catheter assembly 10 is then seated in the aligned receptacles by pressing delivery shaft 28 against protrusions 32 until delivery shaft 28 snaps into delivery shaft receptacle 28. Once seated, a portion of catheter assembly 10 is inclined and distal tip 20 is suspended within reservoir 34.

In another embodiment of the present invention, the method for loading a medical device can include loading a valve prosthesis (not shown) on the distal tip 20 of catheter assembly 10 while the valve prosthesis and distal tip 20 are submerged in reservoir 34. The method can also include implanting a valve prosthesis that was loaded while submerged in reservoir 34. Loading distal tip 20 with the valve prosthesis while submerged in fluid 72, such as a saline solution, in reservoir 34 reduces the risk that the valve prosthesis is contaminated before the valve prosthesis is implanted in the body. Loading distal tip 20 with the valve prosthesis while the catheter assembly 10 is inclined and distal tip 20 is suspended above bottom surface 44 helps a user properly align the prosthesis with distal tip 20 to prevent damage during loading. The method for loading a valve prosthesis can include crimping a valve prosthesis with a crimping device 78 while submerged in reservoir 34.

Figure 6:
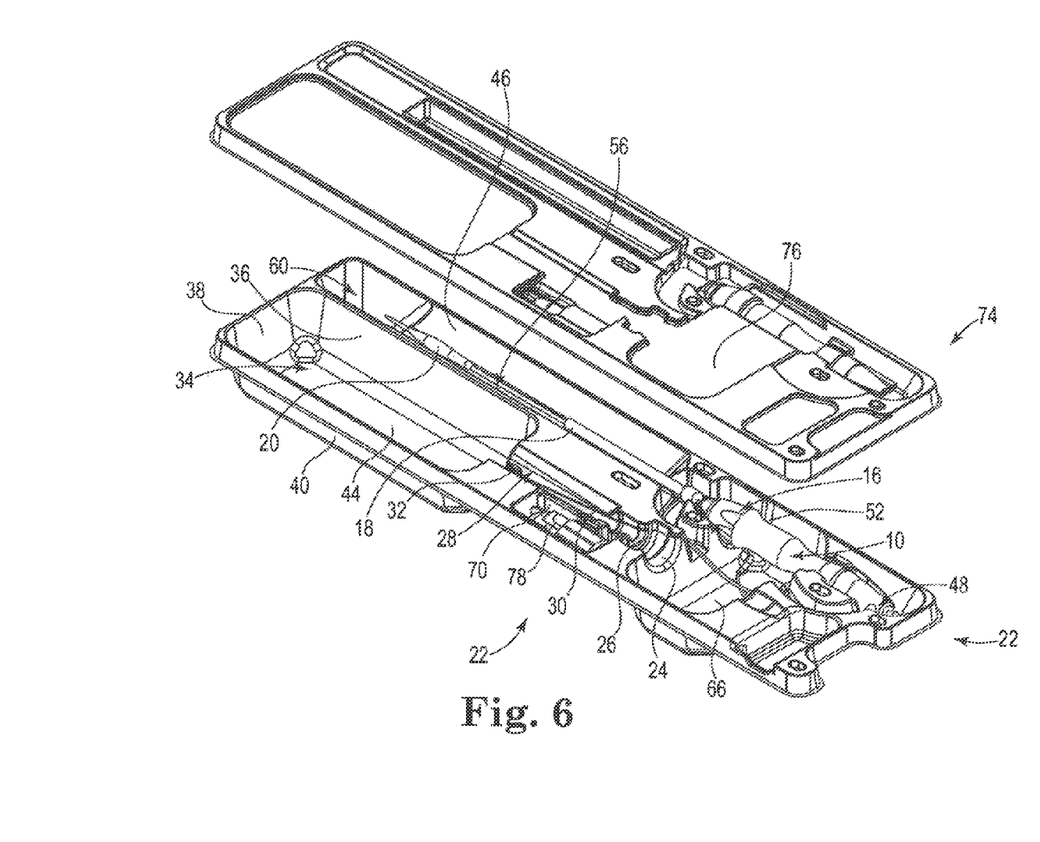
FIG. 6 is a perspective view of the tray of FIGS. 1-5 with the catheter assembly seated therein for transporting.

In another embodiment of the present invention, a method for loading a medical device can include removing catheter assembly 10 from at least one receptacle seating catheter 10 during transport. The at least one transport receptacle is separate from handle assembly receptacle 24, delivery shaft receptacle 28, and reservoir 34. FIG. 6 illustrates an embodiment of tray body 23 with catheter assembly 10 seated within at least one transport receptacle for transporting. The proximal portion of handle assembly 16 is seated in front handle assembly receptacle 48, and the distal portion of handle assembly 16 is seated in back handle assembly receptacle 52. Delivery shaft 28 is seated in elongate delivery shaft receptacle 56, and distal tip 20 is enclosed by distal tip receptacle 60. To seat catheter assembly 10 in tray body 23 for transporting, the proximal portion of handle assembly 16 is aligned with the matching contour of front handle assembly receptacle 48, and the distal portion of handle assembly 16 is aligned with the matching contour of back handle assembly receptacle 52. Delivery shaft 28 is aligned with elongate delivery shaft receptacle 56. Catheter assembly 10 is then seated in the aligned receptacles by pressing the proximal portion of handle assembly 16 against protrusions 51 until handle assembly 16 snaps into front handle assembly receptacle 48.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A tray for use with a medical device and a catheter assembly, the tray comprising:
a tray body comprising:
a loading portion that is configured to restrain the catheter assembly during loading of a medical device on the catheter assembly, the loading portion comprising:
a first receptacle configured to seat a handle assembly of a catheter assembly;
an elongate receptacle configured to seat a delivery shaft of the catheter assembly; and
a reservoir;
wherein a portion of the elongate receptacle slopes downward towards the reservoir; and
a transport portion configured to restrain the catheter assembly during transport, the transport portion being separate from the loading portion, the transport portion comprising at least one receptacle configured to closely seat the catheter assembly.

2. The tray according to claim 1, wherein the at least one receptacle of the transport portion comprises:
a first handle assembly receptacle configured to seat a proximal portion of the handle assembly;
a second handle assembly receptacle configured to seat a distal portion of the handle assembly;
a second elongate receptacle configured to seat the delivery shaft of the catheter assembly; and
a distal tip receptacle configured to enclose a distal tip of the catheter assembly.

3. The tray according to claim 2, wherein the tray body further defines a gripping receptacle configured to allow a user's fingers to wrap around the handle assembly, the gripping receptacle being contiguous to the first receptacle and spaced between the first handle assembly receptacle and the second handle assembly receptacle.

4. The tray according to claim 2, further comprising a lid configured to fit over the tray body when the catheter assembly is seated in the first handle assembly, the second handle assembly, the second elongate receptacle, and the distal tip receptacle.

* * * * *